US010293205B2

(12) United States Patent
Perkins et al.

(10) Patent No.: US 10,293,205 B2
(45) Date of Patent: May 21, 2019

(54) IMU SYSTEM FOR ASSESSING HEAD AND TORSO ORIENTATION DURING PHYSICAL MOTION

(71) Applicant: THE REGENTS OF THE UNIVERSITY OF MICHIGAN, Ann Arbor, MI (US)

(72) Inventors: Noel C. Perkins, Ann Arbor, MI (US); Ryan S. McGinnis, Ann Arbor, MI (US); Brian R. Copple, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 122 days.

(21) Appl. No.: 15/112,515

(22) PCT Filed: Jan. 26, 2015

(86) PCT No.: PCT/US2015/012857
§ 371 (c)(1),
(2) Date: Jul. 19, 2016

(87) PCT Pub. No.: WO2015/112954
PCT Pub. Date: Jul. 30, 2015

(65) Prior Publication Data
US 2016/0339293 A1 Nov. 24, 2016

Related U.S. Application Data

(60) Provisional application No. 61/931,767, filed on Jan. 27, 2014.

(51) Int. Cl.
A61B 5/00 (2006.01)
A61B 5/11 (2006.01)
(Continued)

(52) U.S. Cl.
CPC ............ *A63B 23/0244* (2013.01); *A61B 5/11* (2013.01); *A61B 5/1114* (2013.01);
(Continued)

(58) Field of Classification Search
CPC ...................................................... G01P 1/023
(Continued)

(56) References Cited

U.S. PATENT DOCUMENTS 5,118,102 A * 6/1992 Bahill ....................... G01P 3/00
473/221
5,323,174 A * 6/1994 Klapman ............... G06F 3/0338
345/156
(Continued)

FOREIGN PATENT DOCUMENTS

WO WO-2013080809 A1 6/2013

OTHER PUBLICATIONS

Yuzurihara, Jajime, 'Device Control System, Device Control Method, and Computer-Readable Recording Medium', WO2013080809, Nov. 9, 2012, 75 pages.*

(Continued)

Primary Examiner — Clayton E. LaBalle
Assistant Examiner — Kevin C Butler
(74) Attorney, Agent, or Firm — Harness, Dickey & Pierce, P.L.C.

(57) ABSTRACT

A method and apparatus for monitoring the head and torso orientation of a subject during physical motion. The method and apparatus employ at least two inertial measurement units (IMUs) being temporally synchronized with each other and each measuring three degrees of freedom of angular velocity, acceleration, and optionally magnetic field. A first IMU being affixed to the head of the subject and the second IMU being affixed to the torso of the subject. The orientation of the head, the orientation of the torso, and optionally the (Continued)

BREAKDOWN  BUZZ relative orientation of the head and torso are calculated based on the data from the IMU's and optionally magnetometer data. The resultant output data is transmitted to a host device (computer, tablet, smart phone) and can be used for monitoring, training, coaching, worker safety and health, and/or rehabilitation.

15 Claims, 4 Drawing Sheets

(51) Int. Cl.
  *G01P 1/02* (2006.01)
  *G06K 9/00* (2006.01)
  *A63B 23/02* (2006.01)
  *A63B 71/00* (2006.01)
  *G01P 15/08* (2006.01)
  *G01P 15/18* (2013.01)
  *G01R 33/02* (2006.01)
  *G09B 19/00* (2006.01)
  *G01C 19/5783* (2012.01)

(52) U.S. Cl.
  CPC ........... *A61B 5/1116* (2013.01); *A61B 5/1124* (2013.01); *A61B 5/6803* (2013.01); *A61B 5/6804* (2013.01); *A63B 71/0054* (2013.01); *G01C 19/5783* (2013.01); *G01P 15/18* (2013.01); *G01R 33/0206* (2013.01); *G06K 9/00342* (2013.01); *G09B 19/0038* (2013.01); *A61B 2503/10* (2013.01); *A61B 2562/0219* (2013.01); *A61B 2562/0223* (2013.01); *A63B 2220/40* (2013.01); *A63B 2220/44* (2013.01); *A63B 2225/20* (2013.01); *A63B 2225/50* (2013.01); *A63B 2225/52* (2013.01); *A63B 2243/007* (2013.01); *G01P 1/02* (2013.01); *G01P 1/023* (2013.01); *G01P 15/08* (2013.01)

(58) Field of Classification Search
  USPC .......................................................... 73/493
  See application file for complete search history.

(56) References Cited

U.S. PATENT DOCUMENTS

| | | | | |
|---|---|---|---|---|
| 6,042,492 | A * | 3/2000 | Baum | A63B 24/0003 434/257 |
| 6,533,675 | B2 * | 3/2003 | Funk | A63B 24/0003 473/222 |
| 6,537,076 | B2 * | 3/2003 | McNitt | A63B 24/0003 434/247 |
| 6,821,211 | B2 * | 11/2004 | Otten | A63B 69/3614 473/219 |
| 6,959,259 | B2 * | 10/2005 | Vock | A42B 3/0433 342/104 |
| 7,021,140 | B2 * | 4/2006 | Perkins | A01K 87/00 473/219 |
| 7,234,351 | B2 | 6/2007 | Perkins | |
| 8,955,749 | B2 * | 2/2015 | Elefante | F41G 3/16 235/404 |
| 9,032,794 | B2 | 5/2015 | Perkins et al. | |
| 9,140,717 | B2 * | 9/2015 | Perkins | G01C 21/16 |
| 9,213,889 | B2 * | 12/2015 | Perkins | G06K 9/00342 |
| 9,851,374 | B2 * | 12/2017 | Clark | A63B 71/0619 |
| 2006/0284792 | A1 * | 12/2006 | Foxlin | G02B 27/017 345/8 |
| 2010/0204616 | A1 * | 8/2010 | Shears | A61B 5/1127 600/595 |
| 2011/0025853 | A1 * | 2/2011 | Richardson | H04N 5/2256 348/159 |
| 2011/0109548 | A1 * | 5/2011 | Tu | G06F 3/017 345/158 |
| 2011/0230986 | A1 * | 9/2011 | Lafortune | A43B 3/0005 700/93 |
| 2011/0293129 | A1 * | 12/2011 | Dillen | H04S 7/304 381/370 |
| 2012/0139731 | A1 * | 6/2012 | Razoumov | A61B 5/0022 340/573.1 |
| 2012/0296601 | A1 * | 11/2012 | Eatwell | G01P 15/14 702/141 |
| 2014/0045630 | A1 * | 2/2014 | Perkins | A63B 69/00 473/570 |
| 2015/0314166 | A1 * | 11/2015 | Hong | A63B 71/06 702/151 |
| 2016/0238841 | A1 * | 8/2016 | LaValle | G02B 27/017 |
| 2016/0324461 | A1 * | 11/2016 | Hallberg | A61B 5/4528 |
| 2016/0339293 | A1 * | 11/2016 | Perkins | A61B 5/11 |
| 2017/0153268 | A1 * | 6/2017 | Nahman | G01P 15/135 |
| 2018/0018787 | A1 * | 1/2018 | Giancola | G06T 7/55 |

OTHER PUBLICATIONS

Christina Godvin et al., 'Development of a real-time three-dimensional spinal motion measurement system for clinical practice', Springer, Nov. 11, 2006, 15 pages.*

T. Mirzoev, 'Wireless Transmission of Video for Biomechanical Analysis', Georgia Southern Univeristy, Dec. 2014, pages.*

Mikic, Ivana, 'Human Body Model Acquisition and Tracking using Voxel Data', International Journal of Comuter Vision, 53(3), Jan. 1, 2003, 26 pages.*

Stephanie Blair, 'Biomechanics of Goal-Kicking Accuracy in Australian Football Using an Inertial Measurement System', 35th Conference of the International Society of Biomechanics in Sports, Jun. 14-18, 2017, 4 pages.*

N Shewchenko et al, 'Heading in football. Part 1: Development of biomechanical methods to investigate head response', Br J Sports Medecine, 2005, 16 pages.*

Pedro Nogueira, 'Motion Capture Fundamentals', Programa Doutoral em Engenharia Informática Instituto de Telecomunicações, Nov. 18, 2011, 12 pages.*

Marko Kos and Iztok Kramberger, A Wearable Device and System for Movement and Biometric Data Acquisition for Sports Applications, IEEE Access, vol. 5, May 17, 2017, 10 pages.*

International Search Report and Written Opinion for PCT/US2015/012857, dated May 11, 2015; ISA/KR.

* cited by examiner

US 10,293,205 B2

IMU SYSTEM FOR ASSESSING HEAD AND TORSO ORIENTATION DURING PHYSICAL MOTION

CROSS-REFERENCE TO RELATED APPLICATIONS

This application is a U.S. National Phase Application under 35 U.S.C. 371 of International Application No. PCT/US2015/012857 filed on Jan. 26, 2015 and published as WO 2015/112954 A1 on Jul. 30, 2015. This application claims the benefit of U.S. Provisional Application No. 61/931,767, filed on Jan. 27, 2014. The entire disclosures of the above applications are incorporated herein by reference.

FIELD

The present disclosure relates to an apparatus and method for monitoring the head and torso posture/orientation of a subject during physical motion to evaluate physical performance and/or injury potential.

BACKGROUND AND SUMMARY

This section provides background information related to the present disclosure which is not necessarily prior art. This section provides a general summary of the disclosure, and is not a comprehensive disclosure of its full scope or all of its features.

There are approximately 23,000 non-fatal, football-related traumatic brain injuries that result in emergency room visits in the US annually. In hopes of reducing these numbers, USA Football's newest initiative for promoting the health and safety of developing football players is a program called Heads Up Football. A key component of this initiative is a protocol, Heads Up Tackling[SM], which provides a step-by-step program to teach players proper tackling technique with a focus on reducing head contact and injuries. This program places significant emphasis on maintaining a spine angle of 45° and keeping the head and gaze up, thus shifting the point of contact from the head to the shoulders/chest during a tackle which reduces the likelihood of injury to the brain or spine.

Unfortunately, it is impossible for coaches to accurately and consistently visually monitor the spine and head posture of all their players during a practice or game. One potential solution could be to assess each player's form off the field by reviewing video, but this doesn't help to monitor player safety during a practice or game and provides no objective measurement of body posture. Moreover, the video images do not necessarily provide the quantitative measures of head and torso orientation and importantly the relative orientation of the head to the torso. While video analysis software (e.g. Dartfish) could be used for this need, doing so requires significant post-processing effort from an expert, rendering that method time-consuming and expensive.

According to the present teachings, an alternative technology for monitoring a player's or subject's head and torso posture during physical motion (e.g. play, practice, tackling, training, conditioning, rehabilitation) in real time is provided. This technology, a synchronized array of two or more highly miniaturized, wireless inertial measurement units (IMUs), provides direct measurement of linear acceleration and angular velocity. When secured to the head and torso of an athlete or other subject, data from these devices can be used to monitor the head and torso posture of all players or subjects, in real time, noninvasively on the field of play or other facility. Furthermore, the IMUs can be attached to the player or subject by using body-worn straps, or by directly attaching to or embedding in clothing or sports equipment. For instance, for the sport of football, one IMU may be embedded in a player's helmet secured to the head and a second IMU may be embedded in shoulder pads secured to the player's torso. In so doing, this technique will allow coaches to identify when a player is tackling correctly/incorrectly or otherwise using safe/unsafe technique, will help standardize instruction by augmenting the Heads Up Tackling[SM] protocol, and will ensure that every player on the field is minimizing their chances of head and neck injury to themselves and others.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1A:
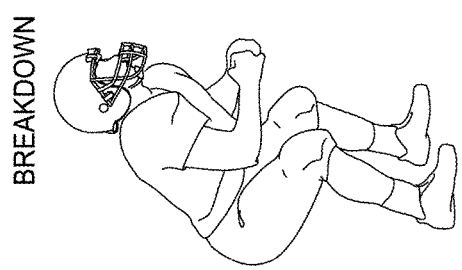
FIGS. 1A-1E illustrate the five phases of the USA Football Heads Up Tackling[SM] protocol.
Figure 1B:
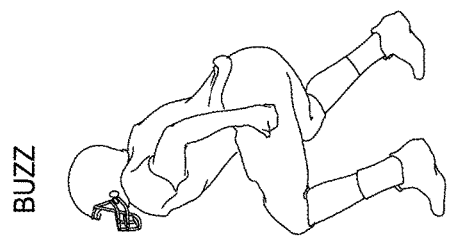
Figure 1C:
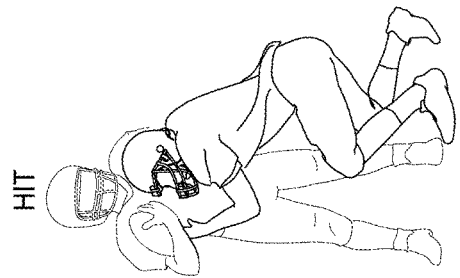
Figure 1D:
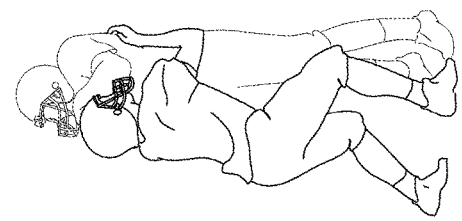
Figure 1E:
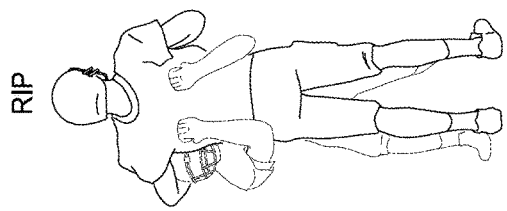

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The present teachings will be discussed in connection with American football play. However, it will be recognized that the principles of the present teachings are equally applicable to a wide variety of applications and sports where the tracking of a player or subject's head and torso can provide beneficial feedback to ascertain proper and/or safe physical motion and performance. In particularly sports applications, proper and safe physical motion can result in improved athletic performance and safety, while decreasing the potential for injury to all players. Moreover, in some embodiments, multiple players or subjects can be monitored simultaneously, thereby providing a means to monitor all players or subjects during the course of practice, training, play, and/or other event. While not exhaustive, examples of such other sports include hockey, rugby, Australian Rules Football, lacrosse, cycling, wrestling, international football (aka soccer), skiing, snow-boarding, mountain climbing, white water rafting, equestrian riding, motor sports, water polo, swimming, among others. Moreover, while not exhaustive, examples of other possible applications include worker safety and health, physical rehabilitation, conditioning, and/or general monitoring.

With particular reference to American football, when teaching tackling, it is generally regarded as good practice to instruct players to hit with their heads up to avoid placing the head at the point of contact during the tackle. For example, Heads Up Tackling$^{SM}$ is USA Football's new tackling training initiative designed to help mitigate many of the traumatic brain and cervical spine injuries resulting from head contact during football play. This technique is a drastic departure from the previous tackling recommendation of hitting with your head "on the ball," still taught by some coaches, which nearly ensures that the head is at, or near, the point of contact during the tackle.

In contrast, the Heads Up Tackling$^{SM}$ protocol suggests breaking the tackle into five phases (breakdown, buzz, hit, shoot, and rip—outlined in FIG. 1) which progress from establishing an initial ready position (breakdown) to actually contacting an opposing player and driving them upwards during the tackle (rip). During all five phases, players are instructed to maintain a 45° angle between their torso and the ground, and to keep the head and gaze facing their target. In theory, this effectively shifts the point of contact from the head to the shoulders/chest during a tackle, reducing the likelihood of injury to the brain or spine. Unfortunately, despite this type of coaching initiative, player reports suggest that it is difficult to maintain a heads up posture all the way through the tackle because of a base instinct to protect the face and eyes at the moment of contact. Teaching player's to overcome this natural instinct requires significant practice time dedicated to correct tackling techniques in game-like situations. Because tackling is such a dynamic motion, assessing correct torso and head posture is difficult for coaches to accomplish visually, and is nearly impossible to accomplish for multiple players simultaneously, thus limiting the efficiency and efficacy of tackling practice. Moreover, visual assessment of tackling technique cannot be standardized because it is necessarily subjective, so two coaches could be teaching the same skills with completely different results. To standardize tackling coaching in football, and allow Heads Up Tackling$^{SM}$ to work as designed, it is necessary to develop a technology for monitoring the posture of the torso and head throughout the tackle, for multiple players, in real time, on the field of play. The principles of the present teachings provide an inexpensive, noninvasive technology and method, centered around the use of highly miniaturized, wireless inertial measurement units (IMUs), ideally suited for accomplishing this task.

Traditionally, in both sports and research contexts, video-based techniques have been used to record a player/subject's motions. In sports contexts, player performance is often analyzed after practices and games by reviewing traditional video records. This technique allows coaches to assess a specific player's behavior while within the field of view of the camera, requires minimal set-up, and analysis of the performance is identical to visual assessment during the practice or game. Unfortunately, these traditional video records have fixed fields of view, are difficult to extract quantitative information of body posture from (especially if the task being analyzed isn't highly constrained), and require an operator to record each video. Quantitative data can be extracted post-recording by using post-processing methods such as that available by Dartfish. However, this post-processing is cumbersome and removes any possibility of the real-time feedback needed to accelerate training on the field of practice/play. Moreover, players often know the time period when they are being recorded which can unduly influence their behavior during that time period.

In research contexts, the posture of the human body is most often quantified using video-based motion capture (MOCAP), which relies on tracking the three-dimensional position of reflective targets or infrared LEDs secured to a subject using an array of high speed cameras arranged around the perimeter of a constrained motion capture volume. This motion capture volume must be precisely calibrated, and markers must be attached to each subject in precise, known locations prior to each use, limiting the number of players that can be simultaneously studied. Following data collection, marker positions must be used as input to a biomechanical model of the subject to extract body posture information. As a result, an operator skilled in marker placement, calibration, and the collection and analysis of marker position data is required for use of this technology. Obviously, this technology again fails to provide the real-time feedback needed to accelerate training on the field of practice/play.

In sum, the current technology available in both sport and research contexts is expensive, can only be used for a small subset of players at any given time, could unduly influence a player's behavior, requires a long data reduction/processing time (not real time), constrains the types of drills being run, and necessitates a skilled operator on hand. For all of these reasons, and more, video-based technologies have limited the acceptance and use of quantitative body posture information during training and play.

Some or all of these shortcomings are addressed by advancing an alternative technology, namely miniaturized, wireless inertial measurement units (IMUs). Miniature, wireless IMUs, which incorporate MEMS accelerometers and angular rate gyros (and optionally magnetometers), measure the translational acceleration and angular velocity of anything to which they are attached, and transmit this data back to a host laptop computer, smart phone, tablet, or similarly enabled device.

Figure 2:
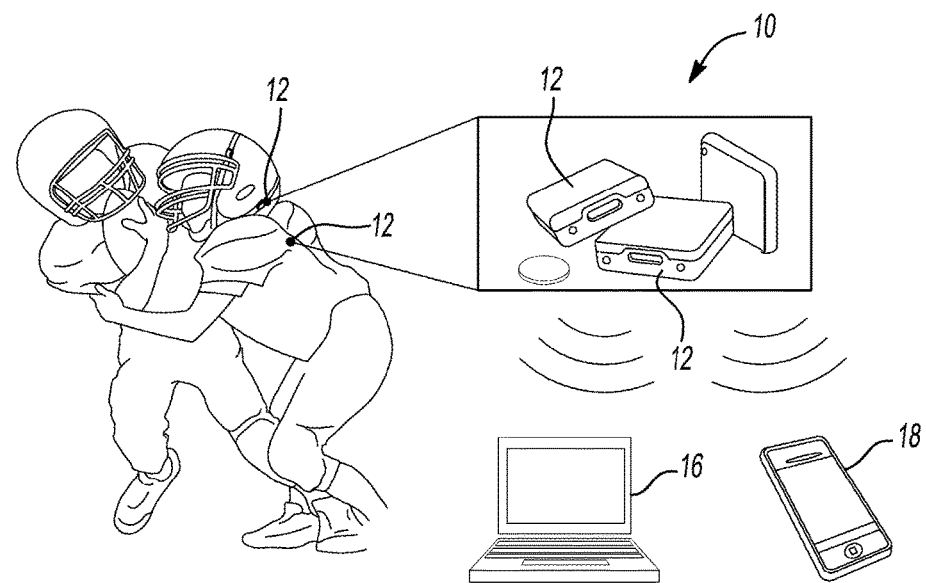
FIG. 2 illustrates an exemplary embodiment of a two-node IMU array, with nodes embedded in the helmet and shoulder pads of the player.
Figure 5:
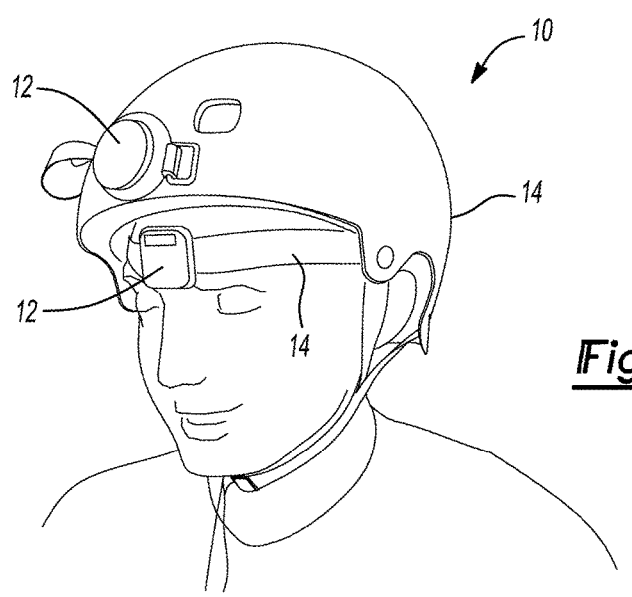
FIG. 5 illustrates the mounting of an IMU to a helmet worn by a subject and, alternatively, to a strap that indexes the IMU against the subject's forehead.

Generally, as illustrated in FIGS. 2 and 5, an apparatus 10 is provided according to the principles of the present teachings having at least two inertial measurement units 12 each measuring three degrees of freedom of angular velocity and three degrees of freedom of acceleration and outputting acceleration data and angular rate gyro data. Each of the inertial measurement units 12 are temporally synchronized such that the acceleration data and angular rate gyro data from each are likewise synchronized. Each of the inertial measurement units 12 are mounted to a respective body segment (e.g. head, torso, and the like) of the player or subject via a mounting system 14 (FIG. 5). Mounting system 14 supports the inertial measurement unit 12 for movement with the mounting system and consequently the associated body segment. A central processing unit 16, which can be separate from the inertial measurement unit 12 or incorporated therewith, receives the acceleration data and the angular rate gyro data from the inertial measurement units and calculates the orientation of the head, the orientation of the torso, and optionally the orientation of the head relative to the torso in response to the acceleration data and the angular rate gyro data from the inertial measurement units and optionally additional magnetometer data and outputs resultant data. A host device 18 receives the resultant data and outputs a response to a user indicative of the head and torso orientation of the subject.

IMU nodes 12 can raw transmit sensor data (i.e., outputs from accelerometer, rate gyro, magnetometer) or processed results (i.e., performance metrics that may include head orientation, torso orientation, relative orientation of head to torso) to the host 18 (i.e., a laptop computer, smart phone, or tablet) for additional data processing and visualization. The transmission may be through wired or wireless means including RF radio protocols (e.g. Bluetooth). The host 18 may display the results visually or provide feedback by other means such as through audible or tactile cues. The host 18 may also enable comparison of player performance metrics to those of an expert or a preferred target. Additionally, the host 18 may enable comparing the current player performance metrics with those measured previously as further means to track player progress.

This technology of the present teachings is inexpensive, does not require the presence of a skilled operator, has no restrictions on field of view or measurement volume, is small and non-invasive which minimizes the effect on player behavior, and is easily scalable for monitoring all players on the field of play. When deployed as a body worn sensor array, synchronized miniature IMUs 12 directly provide the kinematic data needed to estimate the orientation of body segments (e.g. head, torso, legs, arms, and the like) and therefore, as shown in FIG. 2, the torso and head posture of a football player during a tackle.

The MEMS components incorporated in the IMU 12 each provide data to estimate the orientation of the device, and therefore the orientation of the body to which they are attached (in this case the orientation of a player's torso and head). Alone, the orientation estimates from each component are incomplete or error prone. For example, the accelerometer provides a noisy estimate of the IMU's orientation relative to gravity corrupted by the accelerations experienced by the device. In addition, integration of the gyro data provides an independent estimate of the change in the device's orientation subject to a time-varying drift due to integration of small measurement errors and noise. Ultimately, fusing the orientation estimates from each of the components, for example in a complementary or Kalman filtering framework, enables accurate identification of the orientation of the IMU, and therefore accurate tracking of the orientation of the head and torso during tackling.

As discussed herein, to be most useful, the estimates of head and torso orientation should also be synchronized in time as this also enables estimating the orientation of the head relative to the torso and thus the rotations across the cervical spine. To achieve this desired result, the data from two IMU nodes 12 must be time-synchronized by one of several methods, examples of which are presented. One method, achieved through hardware on each node, is to synchronize the clocks embedded in the IMU hardware (e.g. oscillators used to control data sampling and/or overall on-board timing events). This may be achieved by direct communication between the nodes or by communication with a secondary device (such as a host device, ground station, docking station, charging station, etc.) that can establish synchronized clocks. Another method, achieved through experimental protocol, is to incorporate a "synchronization movement" that can be readily identified in the data streams from each IMU node and thus align in time these two data streams. Many synchronization movements may serve this purpose. For instance, commanding the subject to jump results in readily identifiable signatures in the data streams of both sensors as do simultaneous taps on the housings of both sensors. Yet another method would incorporate the output of an external switch or trigger (i.e. an additional electrical signal) that can be simultaneously read or entered into the data streams from both IMU nodes.

Figure 3:
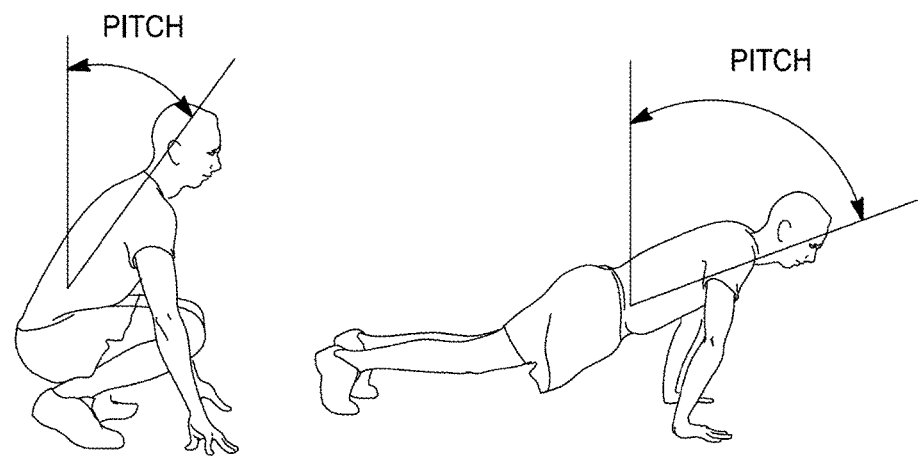
FIG. 3 illustrates the definition of torso pitch angle.

The expected level of accuracy for the orientation estimates is established herein using results from a torso-orientation tracking study. For this study, the orientation of a subject's torso was tracked during an up-down maneuver characteristic of a football player's motion in practice or play. The IMU was affixed to the subject's torso via a strap that firmly pressed the IMU against the sternum. To quantify torso orientation in this example, consider the pitch angle of the torso, which is defined as the angle between a subject's spine and vertical (see FIG. 3). The accuracy of IMU-derived torso pitch angle estimates is established by comparing results to the equivalent quantity derived from motion capture (MOCAP) measurements. The pitch angle from IMU data is computed by fusing accelerometer and angular rate gyro data. In this instance, a complementary filter was used—the use of which should be well understood by those skilled in the art. After establishing torso orientation, calculating pitch angle requires resolving the body-fixed direction of the subject's spine in a ground-fixed reference frame and comparing it to vertical.

To establish the accuracy of the IMU derived torso angle, the IMU and motion capture data were simultaneously recorded during four up-down trials consisting of five get-down motions, where the subject goes from standing to lying prone on the ground as quickly as possible, and five get-up motions, where the subject goes from lying prone to standing as quickly as possible, for each of 16 subjects. The torso pitch angle calculated from IMU and MOCAP data are plotted against time during a representative trial, for one of the subjects, in FIG. 4A. Example "down" and "up" motions are annotated to ease interpretation. The excellent agreement between IMU and MOCAP-derived pitch angle is further confirmed by the correlation plot presented in FIG. 4B. If the pitch angle derived from IMU and MOCAP were identical, the cloud of points would collapse to the black line which has unit slope and zero intercept.

Figure 4A:
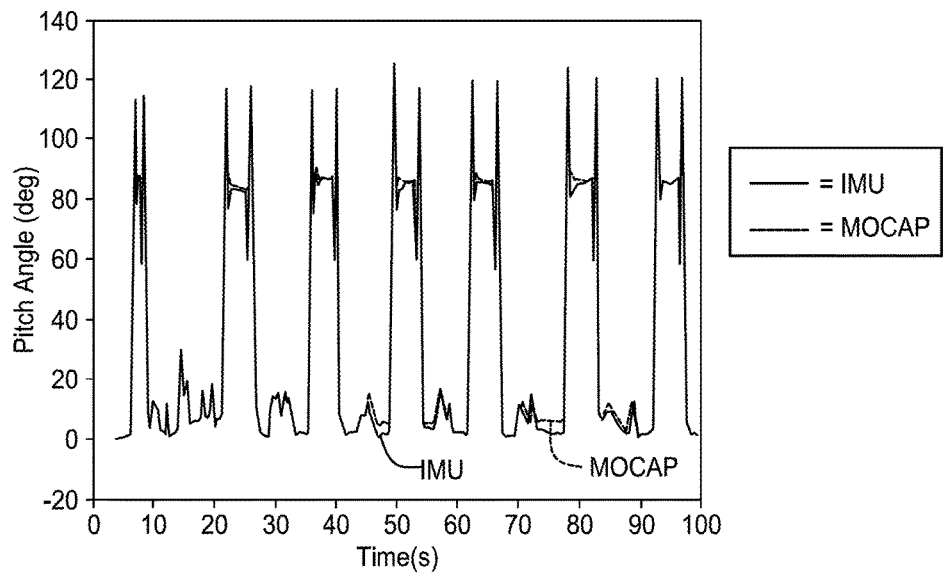
FIG. 4A is a graph of torso pitch angle plotted against time as calculated from the IMU and from MOCAP.
Figure 4B:
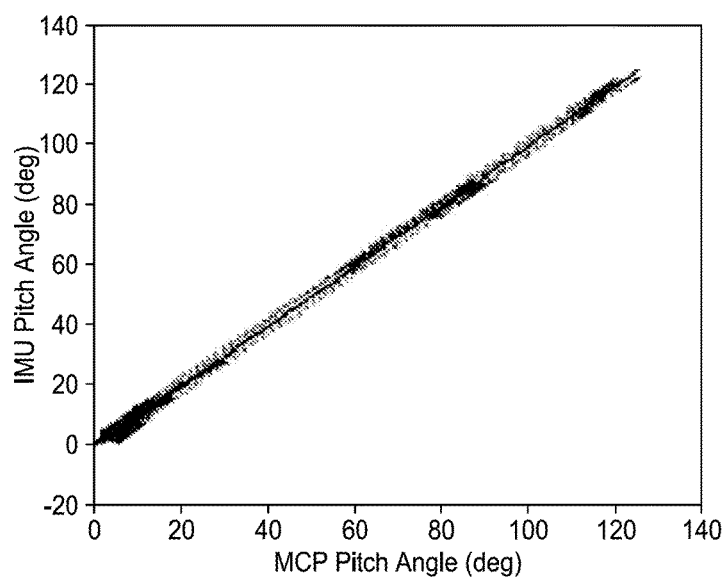
FIG. 4B is a graph plotting IMU pitch angle versus MOCAP pitch angle, where a line with unit slope and zero intercept is plotted for comparison.

Further confirming the excellent qualitative agreement suggested in FIGS. 4A-4B, the mean (standard deviation) of the difference between IMU and MOCAP pitch angle during this trial is 0.75 (1.67)° and a line fit to the data in FIG. 4B has slope of 1.00 with an $R^2$ of 1.00. These results extend to the full data set where the mean (standard deviation) of the mean difference is −0.62 (0.62)°, the standard deviation of the difference is 1.79 (0.86)°, the slope is 0.99 (0.02), and the $R^2$ is 1.00 (0.00) for the 64 trials (4 trials for each of 16 subjects) analyzed.

Figure 6:
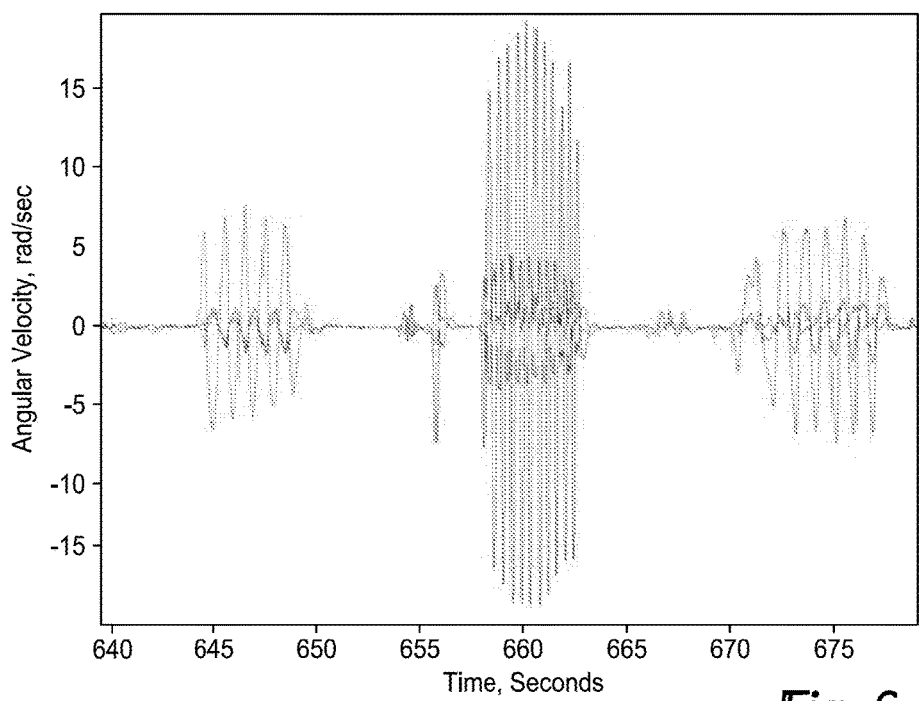
FIG. 6 is a graph plotting the IMU/head angular velocity components versus time for a trial that induces significant head pitching followed by yawing and followed by rolling.

These results demonstrate the excellent accuracy one can expect to achieve with this technology in identifying the orientation of the torso and head during physical motion, such as tackling in football. As a second example, consider the motion of a subject's head as measured using a wireless IMU attached to a worn helmet as shown in FIG. 5. In one embodiment, the IMU is affixed to the exterior shell of the helmet by adhesive and the helmet is secured by a chin strap to the subject's head. In a second embodiment, the IMU is affixed to the subject's forehead by a strap. In all instances, the data from the IMU can be used to resolve the three-dimensional motion of the head including the head orientation. For instance, the sample results of FIG. 6 reveal the (three components) of angular velocity of the head during a trial that includes three primary modes of head motion. These include the repeated nodding of the head in the vertical plane (inducing significant pitch angular velocity), followed by the repeated sideways shaking of the head (inducing significant yaw angular velocity), and ending with the repeated clockwise/counterclockwise rotation of the face (inducing significant roll angular velocity).

The study above demonstrates few of the many possible ways that the IMU nodes can be attached to a subject's head (head-worn mounting system) and torso (body-worn mounting system). By way of example, alternative embodiments may connect the IMU to the torso by a strap that firmly presses the IMU against the torso in locations other than the sternum (e.g. the sacrum, the rib cage) as the exact location of the node on the torso does not alter the ability to deduce the orientation of the torso. Alternatively, the IMU node may be attached to or embedded in equipment or clothing worn on the torso such as athletic shirts (including compression shirts), torso-worn pads (including shoulder pads) and the like. Similarly, and by way of example, the IMU attached to the head may be affixed directly to the head via a strap as in the example above or attached to or embedded in equipment or clothing worn on the head such as in or on the exterior or interior of a helmet, embedded within the helmet, affixed to a cap, or embedded in cap, and the like. Again, the exact location of the node on the head does not alter the ability to deduce the orientation of the head.

The attachment of the IMUs to the torso and head via all embodiments (by straps, via clothing, via equipment) necessarily introduces some compliance between the IMU and the body segment (torso or head) that introduces relative motion between the IMU and the body segment. That relative motion may compromise the objective to track the motion of the body segment. Attaching the IMU directly to the body segment (e.g. via a strap) may minimize that compliance but does not eliminate it given that the soft tissues of the body segment are fundamentally another source of compliance. Nevertheless, the data previously presented (FIGS. 4A-4B) confirms that the IMU can faithfully track the motion of the body segment to the degree required for measuring physical motion and/or athletic performance.

When used to augment USA Football's Heads Up Tackling[SM] protocol, this technology enables coaches to monitor the performance of all their players in real time, non-invasively, on the field of play. This will help to ensure that players use practice time efficiently for developing correct tackling form, helping to protect the head and spine from injury and make football a safer sport for everyone.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An apparatus for athlete development, coaching, or training using real time monitoring of the head and cervical spine orientation of an athlete during physical motion on a field of play, said apparatus comprising:
    at least two inertial measurement units each measuring three degrees of freedom of angular velocity and three degrees of freedom of acceleration and outputting acceleration data and angular rate gyro data, a first of the at least two inertial measurement units being temporally synchronized with a second of the at least two inertial measurement units such that the acceleration data and angular rate gyro data from the first inertial measurement unit and the second inertial measurement unit are temporally synchronized;

a first mounting system supporting the first inertial measurement unit for movement therewith, the first mounting system configured to be connectable to the head of the subject such that the data from the first inertial measurement unit is used to calculate the orientation of the head of the subject;

a second mounting system supporting the second inertial measurement unit for movement therewith, the second mounting system configured to be connectable to the cervical spine of the subject such that the data from the second inertial measurement unit is used to calculate the orientation of the cervical spine of the subject;

a central processing unit configured to receive in real time the acceleration data and the angular rate gyro data from the first and second inertial measurements units, the central processing unit calculating the real time orientation of the head, the real time orientation of the cervical spine, and the real time orientation of the head relative to the cervical spine in response to the acceleration data and the angular rate gyro data from the first and second inertial measurement units during the physical motion on the field of play and outputting resultant real time data; and a host device receiving the resultant real time data and outputting a response to a user on the host device indicative of the real time orientation of the head and the orientation of the cervical spine of the athlete on the field of play.

2. The apparatus according to claim 1 wherein at least one of the at least two inertial measurement units measures a local magnetic field and outputs magnetometer data, wherein the central processing unit calculates the real time orientation of the head, the real time orientation of the cervical spine, and the real time orientation of the head relative to the cervical spine in response to the acceleration data, the angular rate gyro data, and the magnetometer data.

3. The apparatus of claim 1, further comprising:

a magnetometer measuring a local magnetic field and outputting magnetometer data, the magnetometer being separate from the first and second inertial measurement units, wherein the central processing unit calculates the real time orientation of the head, the real time orientation of the cervical spine, and the real time orientation of the head relative to the cervical spine in response to the acceleration data and the angular rate gyro data from the first and second inertial measurement units and the magnetometer data from the magnetometer.

4. The apparatus according to claim 1, further comprising:

a transmission system operably coupled between the first and second inertial measurement units and the central processing unit, the transmission system transmitting the acceleration data and the angular rate gyro data from the first and second inertial measurement units to the central processing unit.

5. The apparatus according to claim 4 wherein the transmission system is wireless.

6. The apparatus according to claim 1, further comprising:

a transmission system operably coupled between the central processing unit and the host device, and the transmission system transmitting at least the resultant data to the host device.

7. The apparatus according to claim 6 wherein the transmission system is wireless.

8. The apparatus according to claim 6 wherein the transmission system transmits the acceleration data and the angular rate gyro data from the first and second inertial measurement units and the resultant data to the host device.

9. The apparatus according to claim 1 wherein the first mounting system includes a helmet worn by the subject, the first inertial measurement unit being fixedly attached to or embedded with the helmet.

10. The apparatus according to claim 1 wherein the second mounting system includes a body-worn mounting system worn by the subject, the second inertial measurement unit being fixedly attached to or embedded with the body-worn mounting system.

11. The apparatus according to claim 1 wherein the host device is a computer, tablet, smart phone, or CPU-enabled devices, wherein the output of the host device is delivered in visual, audible, or tactile forms.

12. A method for athlete development, coaching, or training using real time monitoring of the head and cervical spine orientation of an athlete during physical motion on a field of play, said method comprising:

employing at least two inertial measurement units each measuring three degrees of freedom of angular velocity and three degrees of freedom of acceleration and outputting acceleration data and angular rate gyro data, a first of the at least two inertial measurement units being temporally synchronized with a second of the at least two inertial measurement units such that the acceleration data and angular rate gyro data from the first inertial measurement unit and the second inertial measurement unit are temporally synchronized;

affixing the first inertial measurement unit to the head of the athlete for movement therewith;

affixing the second inertial measurement unit to the torso of the athlete within a cervical spine region for movement therewith;

calculating the real time orientation of the head, the real time orientation of the cervical spine, and the real time orientation of the head relative to the cervical spine in response to the acceleration data and the angular rate gyro data from the first and second inertial measurement units during the physical motion on the field of play and outputting resultant real time data; and receiving the resultant real time data by a host device and outputting a response to a user on the host device indicative of the real time orientation of the head and the orientation of the cervical spine of the athlete on the field of play, using the response on the host device for athlete development, coaching, or training.

13. The method according to claim 12, further comprising:

employing a magnetometer measuring a local magnetic field and outputting magnetometer data, and calculating the real time orientation of the head, the real time orientation of the cervical spine, and the real time orientation of the head relative to the cervical spine in response to the acceleration data, the angular rate gyro data, and the magnetometer data.

14. The method according to claim 13 wherein the magnetometer is separate from the at least two inertial measurement units.

15. A method for athlete development, coaching, or training using real time monitoring of the head and cervical spine orientation of a plurality of athletes during physical motion on a field of play, said method comprising:

employing at least two inertial measurement units for each of the plurality of athletes, each of the inertial measurement units measuring three degrees of freedom of angular velocity and three degrees of freedom of acceleration and outputting acceleration data and angular rate gyro data, a first of the at least two inertial measurement units being temporally synchronized with a second of the at least two inertial measurement units such that the acceleration data and angular rate gyro data from the first inertial measurement unit and the second inertial measurement unit are temporally synchronized;

affixing the first inertial measurement unit to the head of each of the plurality of athletes for movement therewith;

affixing the second inertial measurement unit to the torso of each of the plurality of athletes within a cervical spine region for movement therewith;

calculating the real time orientation of the head, the real time orientation of the cervical spine, and the real time orientation of the head relative to the cervical spine of each of the plurality of athletes in response to the acceleration data and the angular rate gyro data from the first and second inertial measurement units during the physical motion on the field of play and outputting resultant real time data for each of the plurality of athletes; and receiving the resultant real time data for each of the plurality of athletes by a host device and outputting a response to a user on the host device indicative of at least one of the real time orientation of the head, the real time orientation of the cervical spine, and the real time orientation of the head relative to the cervical spine of each of the plurality of athletes on the field of play, using the response on the host device for athlete development, coaching, or training.

* * * * *